(12) United States Patent
Chida et al.

(10) Patent No.: US 11,589,894 B2
(45) Date of Patent: Feb. 28, 2023

(54) MEDICAL DEVICE

(71) Applicant: TERUMO KABUSHIKI KAISHA, Tokyo (JP)

(72) Inventors: Takahiro Chida, Cupertino, CA (US); Yuichi Tada, Cupertino, CA (US)

(73) Assignee: TERUMO KABUSHIKI KAISHA, Tokyo (JP)

( * ) Notice: Subject to any disclaimer, the term of this patent is extended or adjusted under 35 U.S.C. 154(b) by 370 days.

(21) Appl. No.: 16/998,824

(22) Filed: Aug. 20, 2020

(65) Prior Publication Data

US 2021/0093348 A1    Apr. 1, 2021

(30) Foreign Application Priority Data

Sep. 30, 2019    (JP) .............................. JP2019-179470

(51) Int. Cl.
*A61B 17/3207* (2006.01)
*A61B 17/00* (2006.01)

(52) U.S. Cl.
CPC .................. *A61B 17/320758* (2013.01); *A61B 2017/00867* (2013.01); *A61B 2217/005* (2013.01)

(58) Field of Classification Search
CPC .......... A61B 17/3207; A61B 17/32037; A61B 17/320725; A61B 17/32075; A61B 17/320783; A61B 17/320758; A61B 2017/320024; A61B 2017/320775

See application file for complete search history.

(56) References Cited

U.S. PATENT DOCUMENTS

| | | | |
|---|---|---|---|
| 2009/0234378 A1* | 9/2009 | Escudero | ....... A61B 17/320758 606/159 |
| 2011/0196402 A1* | 8/2011 | Robertson | .............. A61N 7/022 606/169 |
| 2017/0273698 A1* | 9/2017 | McGuckin, Jr. | .............................. A61B 17/320758 |
| 2018/0353199 A1 | 12/2018 | Tada et al. | |

* cited by examiner

*Primary Examiner* — Tuan V Nguyen
(74) *Attorney, Agent, or Firm* — Kim & Stewart LLP

(57) ABSTRACT

A medical device is capable of aspirating an object in a body lumen, while preventing the retention of the object therein, and effectively discharging the object. The medical device includes: a rotatable drive shaft having a lumen; a cutting portion fixed to a distal portion of the drive shaft to cut the object; and a housing that contains a proximal portion of the drive shaft and has a discharge port through which the cut object is discharged. The drive shaft has a proximal opening portion that extends around a portion of a circumference of the drive shaft to expose a discharge opening. The discharge port includes a discharge hole through which the cut object discharged through the discharge opening of the proximal opening portion is discharged from the housing, and a guide surface that protrudes toward the proximal opening portion to guide the cut object into the discharge hole.

19 Claims, 5 Drawing Sheets

MEDICAL DEVICE

CROSS-REFERENCE TO RELATED APPLICATION(S)

This application is based upon and claims the benefit of priority from Japanese Patent Application No. 2019-179470, filed on Sep. 30, 2019, the entire contents of which are incorporated herein by reference.

BACKGROUND OF THE INVENTION

Field of the Invention

The present invention relates to a medical device for removing an object in a body lumen.

Background Art

Methods for treating a stenosed site due to plaque or thrombus in a blood vessel include a method of inflating the blood vessel with a balloon and a method of indwelling a mesh-like or coil-like stent in the blood vessel as a support for the blood vessel. However, it is difficult for these methods to treat the stenosed site that is hardened by calcification or a stenosed site that occurs at a branching portion of a blood vessel. A method that makes treatment possible even in such a case is a method for cutting and removing a stenosis object such as plaque and thrombus.

For example, US Patent No. 2018/0353199 describes a device in which a cutter for cutting an object is fixed to a distal portion of a drive shaft. The device rotates the drive shaft and allows the cutter to cut the object. The device includes a housing having a discharge port through which an aspiration force is applied, at a handle thereof. The debris formed by cutting is aspirated into a lumen through a distal opening portion of the drive shaft and moved to a proximal side. Thereafter, the debris moves into the housing through a discharge hole on the drive shaft and is then discharged through the discharge port.

The debris is easily spread around the outer periphery of the rotating drive shaft within the housing. When the debris blocks the opening portion on the proximal side of the drive shaft, the debris is retained in the housing and is less likely to be discharged to the outside through the discharge port.

SUMMARY OF THE INVENTION

Embodiments solve the above-described problems, and provide a medical device capable of aspirating an object in a body lumen, preventing retention of the object in the device, and effectively discharging the object.

According to an embodiment, there is provided a medical device for removing an object in a body lumen, including: a rotatable drive shaft having a lumen; a cutting portion fixed to a distal portion of the drive shaft to cut the object; and a housing that contains a proximal portion of the drive shaft and has a discharge port above the proximal portion of the drive shaft and through which the cut object is discharged. The drive shaft has a proximal opening portion that extends around a portion of a circumference of the drive shaft to expose a discharge opening for the cut object. The discharge port includes a discharge hole through which the cut object discharged through the discharge opening of the proximal opening portion is discharged from the housing, and a guide surface that protrudes toward the proximal opening portion to guide the cut object to the discharge hole.

According to another embodiment, there is provided a medical device for removing an object in a body lumen, including: a rotatable drive shaft having a lumen; and a housing that contains a proximal portion of the drive shaft and has a discharge port through which the cut object is discharged. The drive shaft has a proximal opening portion that extends around a portion of a circumference of the drive shaft to expose a discharge opening for the cut object. The discharge port includes a discharge hole through which the cut object discharged through the discharge opening of the proximal opening portion is discharged from the housing, and a guide surface that protrudes toward the proximal opening portion to guide the cut object to the discharge hole.

According to still another embodiment, there is provided a medical device for removing an object in a body lumen, including: a rotatable drive shaft having a lumen; a cutting portion fixed to a distal portion of the drive shaft to cut the object; and a housing that contains a proximal portion of the drive shaft and has a discharge port through which the cut object is discharged. The drive shaft has a proximal opening portion that extends around a portion of a circumference of the drive shaft to expose a discharge opening for the cut object. The discharge port includes a discharge hole on a surface of the discharge port that faces a direction that is opposite to a moving direction of the drive shaft at a top of the drive shaft and through which the cut object discharged through the discharge opening of the proximal opening portion is discharged from the housing.

The medical device configured as described above can effectively guide the object that is discharged through the proximal opening portion and rotates, to the discharge hole of the discharge port. Therefore, the proximal opening portion of the drive shaft is prevented from being completely blocked by the object. Therefore, the medical device can aspirate the object in the body lumen, prevent the retention of the object in the device, and effectively discharge the object.

BRIEF DESCRIPTION OF THE DRAWINGS

FIG. 3(A) is a cross-sectional view viewed from a distal side, and FIG. 3(B) is a cross-sectional view taken along line A-A of FIG. 3(A).

FIG. 5(A) is a cross-sectional view viewed from the distal side, and FIG. 5(B) is a cross-sectional view taken along line B-B of FIG. 5(A).

FIG. 6(A) is a cross-sectional view viewed from the distal side, and FIG. 6(B) is a cross-sectional view taken along line C-C of FIG. 6(A).

FIG. 7(A) is a cross-sectional view viewed from the distal side, and FIG. 7(B) is a plan view taken along line D-D of FIG. 7(A).

DETAILED DESCRIPTION OF THE INVENTION

Figure 1:
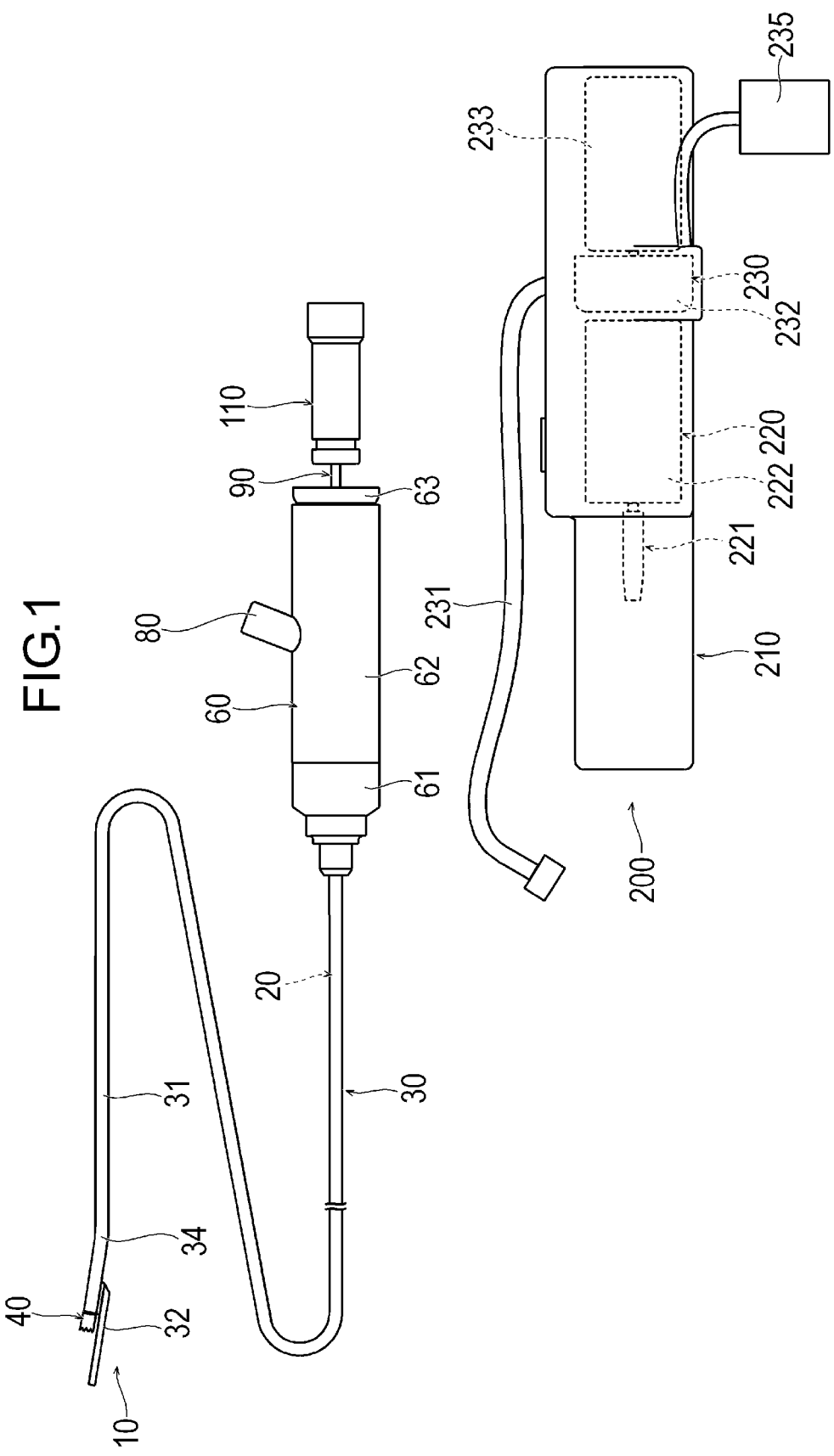
FIG. 1 is a plan view illustrating a medical device and a drive device according to a first embodiment.

Hereinafter, embodiments will be described with reference to the drawings. In some cases, the sizes and ratios of the respective members in the drawings may be exaggerated for convenience of description and may differ from the actual sizes and ratios.

First Embodiment

In acute lower limb ischemia or deep venous thrombosis, a medical device 10 according to a first embodiment is inserted into a blood vessel and is used for a procedure to cut and remove thrombus, plaque, atheroma, calcified lesion, and the like. In the present specification, a side of the device which is inserted into a blood vessel is referred to as a "distal side", and a hand-side of the device which is operated by a user is referred to as a "proximal side". Further, an object to be removed is not necessarily limited to thrombus, plaque, atheroma, or calcified lesion, and may include any object that can be present in the body lumen.

Figure 2:
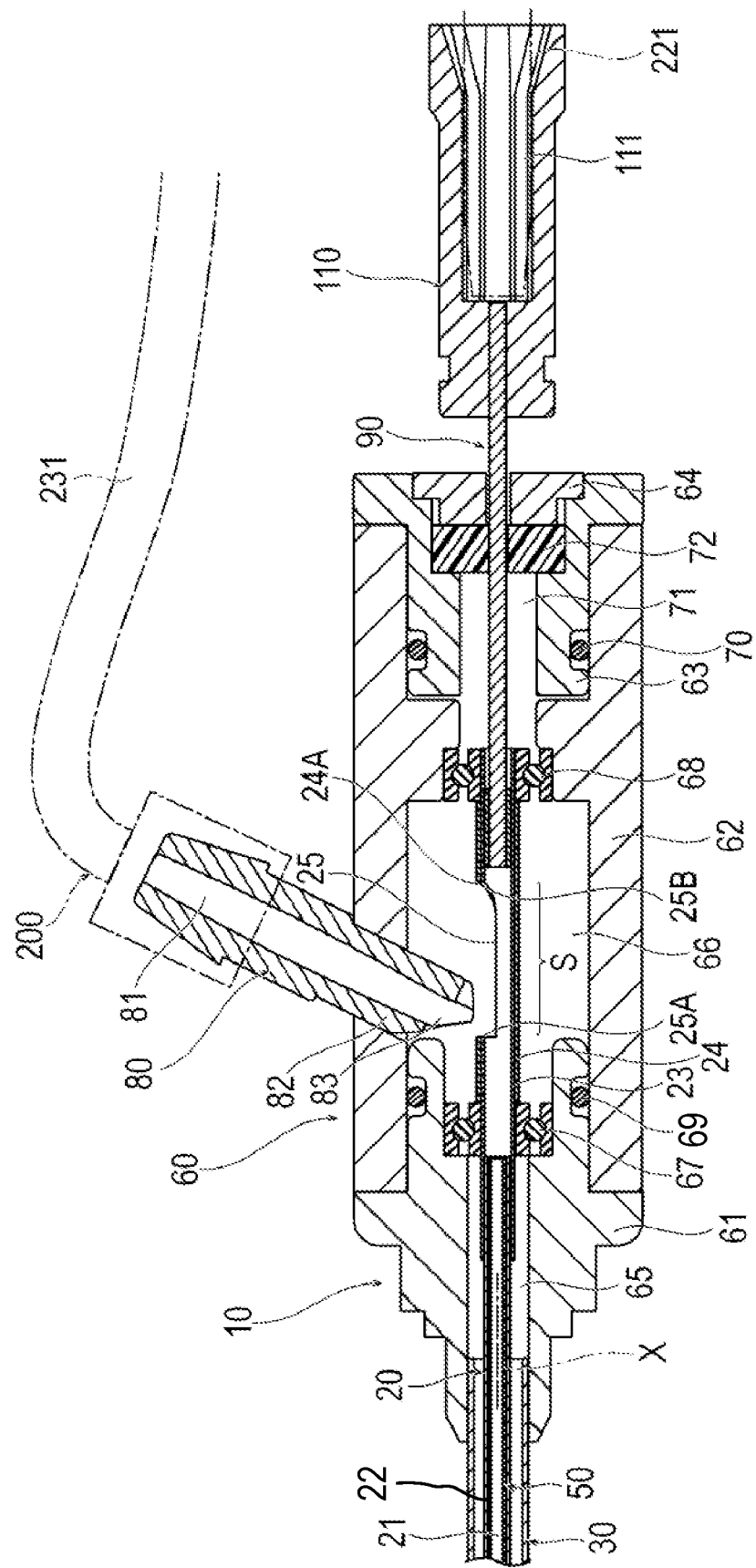
FIG. 2 is a cross-sectional view illustrating a proximal portion of the medical device according to the first embodiment.

As illustrated in FIGS. 1 and 2, the medical device 10 is interlocked with and driven by a drive device 200 that generates a driving force and an aspiration force. The medical device 10 includes an elongated drive shaft 20 that is rotationally driven, an outer tube 30 that contains the drive shaft 20, and a cutting portion 40 that cuts the object. The medical device 10 further includes an inner tube 50 disposed on the inside of the drive shaft 20, and a proximal shaft 90 fixed to a proximal portion of the drive shaft 20. The medical device 10 further includes a housing 60 that contains the proximal portion of the drive shaft 20 which is rotatable therein, and a rotation input unit 110 that receives a rotational force from the drive device 200.

Figure 4:
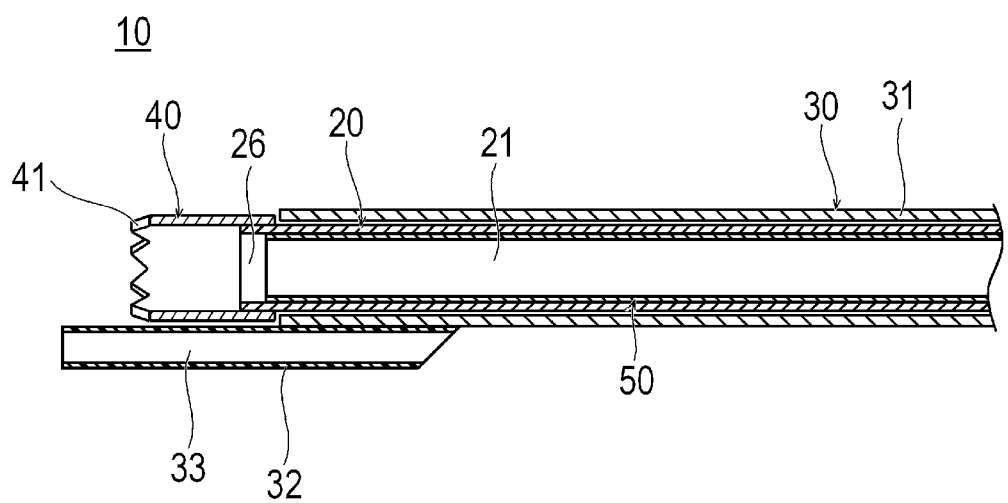
FIG. 4 is a cross-sectional view illustrating a distal portion of the medical device according to the first embodiment.

The drive shaft 20 transmits the rotational force to the cutting portion 40. The drive shaft 20 is formed with an aspiration lumen 21 through which the cut object is moved to the proximal side. The drive shaft 20 includes an elongated drive shaft main body 22, a drive shaft proximal portion 23 fixed to a proximal portion of the drive shaft main body 22, and an auxiliary member 24. The drive shaft 20 penetrates the outer tube 30, and the cutting portion 40 is fixed to a distal portion. The proximal portion of the drive shaft 20 is positioned inside of the housing 60. The proximal portion of the drive shaft 20 is interlocked with the proximal shaft 90. As illustrated in FIG. 4, the drive shaft 20 has a distal opening portion 26 at which the aspiration lumen 21 opens, at a distal end thereof. The distal opening portion 26 is an entrance into which debris, which is an aspiration target to be formed by cutting, enters. The drive shaft 20 has a proximal opening portion 25 at the proximal portion thereof. The proximal opening portion 25 is an outlet through which the debris that has entered the drive shaft 20 through the distal opening portion 26 is discharged. The proximal opening portion 25 is formed by cutting out a part of the drive shaft 20 in the circumferential direction. The proximal opening portion 25 is formed in the proximal portion of the drive shaft 20 to penetrate the inner wall surface and the outer wall surface of the drive shaft 20. Therefore, the proximal opening portion 25 opens toward a side (in a direction orthogonal to a central axis X of the drive shaft 20). The proximal opening portion 25 has a length S in the axial direction of the drive shaft 20. An edge portion 25A on the distal side of the proximal opening portion 25 is formed substantially perpendicular to the central axis X. An edge portion 25B on the proximal side of the proximal opening portion 25 is formed by an arc that is convex toward the proximal side.

The drive shaft main body 22 has the characteristics of being flexible and capable of transmitting rotational power applied from the proximal side to the distal side.

The drive shaft proximal portion 23 has a substantially circular tube shape and has the proximal opening portion 25 formed therein. A distal portion of the drive shaft proximal portion 23 covers the outer peripheral surface of the proximal portion of the drive shaft main body 22 and is fixed to the drive shaft main body 22. Alternatively, the distal portion of the drive shaft proximal portion 23 may be inserted into the proximal portion of the drive shaft main body 22 and fixed to the drive shaft main body 22. In addition, the distal end surface of the drive shaft proximal portion 23 may abut against and be fixed to the proximal end surface of the drive shaft main body 22. The drive shaft proximal portion 23 is rotatably supported on the inside of the housing 60, by a first bearing 67 and a second bearing 68 which will be described later. Therefore, the drive shaft 20 can rotate smoothly at high speeds. The form of the drive shaft 20 is not limited in any way as long as the drive shaft 20 can transmit the rotational power and has the lumen and the proximal opening portion 25. The drive shaft 20 may be integrally formed without being divided into the drive shaft main body 22 and the drive shaft proximal portion 23.

The auxiliary member 24 having a shorter length along the central axis X than that of the drive shaft proximal portion 23 covers the outer peripheral surface of the drive shaft proximal portion 23, and is fixed thereto. The auxiliary member 24 has a substantially circular tube shape. The auxiliary member 24 is formed with an opening portion having a shape substantially the same as that of the proximal opening portion 25 at a position that overlaps the proximal opening portion 25. The distal end surface of the auxiliary member 24 abuts against the first bearing 67 that supports the drive shaft proximal portion 23. The proximal end surface of the auxiliary member 24 abuts against the second bearing 68 that supports the drive shaft proximal portion 23. Therefore, the auxiliary member 24 appropriately sets the positions of the first bearing 67 and the second bearing 68 with respect to the drive shaft proximal portion 23. The auxiliary member 24 also reinforces the drive shaft proximal portion 23 in which the proximal opening portion 25 is formed. The auxiliary member 24 is optional and need not be provided.

A distal portion of the proximal shaft 90 enters the lumen of the drive shaft proximal portion 23 from the proximal side and is fixed to the drive shaft proximal portion 23. The rotation input unit 110 that receives the rotational force from the drive device 200 is fixed to a proximal portion of the proximal shaft 90. The proximal portion of the proximal shaft 90 protrudes from the housing 60 to the proximal side.

The material of the drive shaft main body 22 is not particularly limited, and, for example, stainless steel, polyolefin such as Ta, Ti, Pt, Au, W, polyethylene, and polypropylene, polyester such as polyamide and polyethylene terephthalate, fluorine-based polymer such as ETFE, polyether ether ketone (PEEK), polyimide, and the like can be preferably used. Further, the drive shaft main body 22 may be made of a plurality of materials, and a reinforcing member such as a wire rod may be embedded therein.

The materials of the drive shaft proximal portion 23, the auxiliary member 24, and the proximal shaft 90 are not particularly limited, and, for example, stainless steel, Ta, Ti, Pt, Au, W, shape memory alloy and the like can be preferably used. The materials of the drive shaft proximal portion 23, the auxiliary member 24, and the proximal shaft may be resins such as engineering plastics such as polyether ether ketone (PEEK).

As illustrated in FIG. 2, the rotation input unit 110 is a substantially columnar member fixed to a proximal end of the drive shaft 20. The rotation input unit 110 is a member that is interlocked with a rotary drive shaft 221 of the drive device 200 and receives rotational power therefrom. A proximal portion of the rotation input unit 110 includes a fitting concave portion 111 into which the rotary drive shaft 221 is fitted.

As illustrated in FIGS. 2 and 4, the inner tube 50 is a flexible pipe body and is disposed on the inside of the drive shaft 20. The inner tube 50 prevents damage to the inner peripheral surface of the drive shaft 20 due to debris that flows on the inside of the drive shaft 20. The inner tube 50 may be fixed (and alternatively, not fixed) to the inner peripheral surface of the drive shaft 20. The inner tube 50 is optional and need not be provided.

As illustrated in FIGS. 1, 2, and 4, the outer tube 30 includes an outer tube main body 31 that contains the drive shaft 20 so that the drive shaft 20 is rotatable therein, and a distal tube 32 that is fixed to the side surface of a distal portion of the outer tube main body 31.

The outer tube main body 31 is a flexible pipe body, and a proximal portion is fixed to the housing 60. The distal portion of the outer tube main body 31 is positioned on the proximal side of the cutting portion 40. The distal tube 32 is a flexible pipe body, and is fixed to the outer peripheral surface of the distal portion of the outer tube main body 31. The distal tube 32 has a guide wire lumen 33 into which a guide wire can be inserted.

As illustrated in FIGS. 1 and 4, the cutting portion 40 is a member that cuts and reduces the size of an object such as thrombus, plaque, or calcified lesion. Therefore, "cutting" means applying a force to an object and reducing the size of the object. The method of applying the force in cutting and the shape and form of the object after cutting are not limited. The cutting portion 40 has a strength capable of cutting the above-described object. The cutting portion 40 is fixed to the outer peripheral surface of the distal portion of the drive shaft 20. The proximal end surface of the cutting portion 40 may be fixed to the distal end surface of the drive shaft 20. The cutting portion 40 is a cylinder that protrudes toward the distal side from the drive shaft 20. The distal end of the cutting portion 40 is provided with a sharp blade 41. The shape of the blade 41 is not limited to any particular shape. The cutting portion 40 may have a large number of fine abrasive grains instead of the blade 41.

As illustrated in FIGS. 1 and 2, the housing 60 includes a first part 61 disposed on the distal side, a second part 62 disposed substantially at the center, a third part 63 disposed on the proximal side, and a fourth part 64. The housing 60 further has a discharge port 80 to which an aspiration tube 231 of the drive device 200, which will be described later, can be connected.

The first part 61 is interlocked with a distal portion of the second part 62. A first sealing unit 69 that seals the internal space is disposed between the first part 61 and the second part 62. The first part 61 has a first internal space 65 through which the drive shaft 20 penetrates and within which the drive shaft 20 rotates. The proximal portion of the outer tube main body 31 is fixed to the inner peripheral surface on the distal side of the first internal space 65.

The second part 62 is positioned on the proximal side of the first part 61. The second part 62 has a second internal space 66 in which the drive shaft 20 and the proximal shaft 90 are contained for rotation therein. The discharge port 80 is inserted and interlocked with the hole which penetrates the second part 62 through the outer wall surface to the inner wall surface of the second part 62. The first bearing 67 and the second bearing 68 are arranged on the inner wall surface of the second internal space 66. The inner peripheral surface of the first bearing 67 is in contact with the outer peripheral surface of the drive shaft proximal portion 23 on the distal side of the proximal opening portion 25. The inner peripheral surface of the second bearing 68 is in contact with the outer peripheral surface of the drive shaft proximal portion 23 on the proximal side of the proximal opening portion 25. Therefore, the drive shaft 20 and the proximal shaft 90 are rotatably supported by the first bearing 67 and the second bearing 68, and can rotate smoothly at high speeds. The positions where the first bearing 67 and the second bearing 68 are arranged are not limited to the positions described herein. For example, the first bearing 67 and/or the second bearing 68 may be fixed to the outer peripheral surface of the proximal shaft 90. Further, the first bearing 67 and/or the second bearing 68 are optional and need not be provided.

The third part 63 is interlocked with a proximal portion of the second part 62. The third part 63 has a third internal space 71 through which the proximal shaft 90 penetrates for rotation therein. A second sealing unit 70 that seals the internal space is disposed between the second part 62 and the third part 63.

The fourth part 64 is interlocked with a proximal portion of the third part 63. The fourth part 64 holds a third sealing unit 72 disposed between the third part 63 and the proximal shaft 90 in a predetermined space of the third part 63. The third sealing unit 72 allows the proximal shaft 90 to rotate while sealing the third internal space 71.

The proximal opening portion 25 of the drive shaft 20 is positioned in the second internal space 66. Therefore, the negative pressure applied to the discharge port 80 from the aspiration tube 231 acts on the interior space of the drive shaft 20 from the proximal opening portion 25. The first sealing unit 69, the second sealing unit 70, and the third sealing unit 72 prevent the negative pressure in the first internal space 65, the second internal space 66, and the third internal space 71 from escaping.

Figure 3:
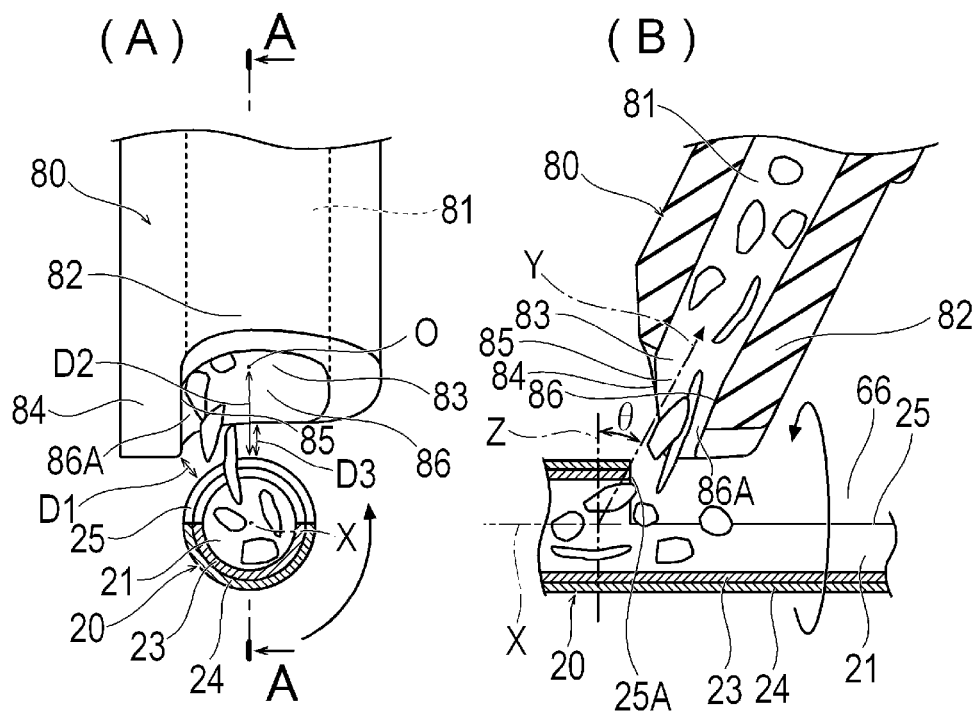
FIG. 3 is a view illustrating a proximal portion of a drive shaft and a discharge port according to the first embodiment.

As illustrated in FIGS. 2 and 3, the discharge port 80 has a substantially cylindrical shape, a first end portion thereof is positioned on the outside of the housing 60, and a second end portion thereof protrudes into the second internal space 66 of the housing 60. The discharge port 80 is formed with a passage 81 that extends from the first end portion to the second end portion. A discharge hole 83 for aspirating debris and a protruding portion 84 are formed at an end portion 82 of the discharge port 80, which protrudes into the second internal space 66. It should be noted that the space into which the end portion 82 protrudes does not have to be the second internal space 66 as long as the space is in the housing 60. The discharge hole 83 is positioned at the end portion of the passage 81 where the inner wall is formed around the entire circumference (360 degrees) of the passage 81. The discharge hole 83 opens toward the proximal opening portion 25. In other words, at least a part of the proximal opening portion 25 intersects an extension of the passage 81 past the discharge hole 83. Further, the discharge hole 83 preferably overlaps at least a part of the length S along which the proximal opening portion 25 is positioned in the axial direction of the drive shaft 20. In addition, the discharge hole 83 preferably overlaps a distal portion of the proximal opening portion 25 in the axial direction of the drive shaft 20. The position of the discharge hole 83 is not limited to any particular location. The position of the proximal opening portion 25 of the drive shaft 20 is not limited to any particular location as long as the negative pressure from the discharge hole 83 can be applied thereto.

An angle θ formed on the proximal side by the extending direction Y of the passage 81 that extends outward from the discharge hole 83 of the discharge port 80 with respect to a plane Z orthogonal to the central axis X of the drive shaft 20 is not limited to any particular angle, and, for example, the angle is 0 to 90 degrees, preferably more than 0 degrees and less than 90 degrees, more preferably 30 to 60 degrees. When the angle θ is more than 0 degrees and less than 90 degrees, the extending direction Y of the passage 81 is inclined to the proximal side with respect to the plane Z. Therefore, the discharge hole 83 and the passage 81 can smoothly receive and discharge the debris that is discharged while moving in the proximal direction from the proximal opening portion 25 without significantly changing the direction. However, it should be noted that the extending direction Y of the passage 81 may be inclined to the distal side with respect to the plane Z. The inner diameters of the discharge hole 83 and the passage 81 preferably have a size by which the debris can be discharged. As an example, in a case where the outer diameter of the part of the drive shaft 20 at which the proximal opening portion 25 is formed is 2.0 mm and the inner diameter is 1.0 mm, the inner diameters of the discharge hole 83 and the passage 81 are, for example, 1.6 mm.

As illustrated in FIG. 3, the protruding portion 84 protrudes from the discharge hole 83 in the direction toward the drive shaft 20. The protruding portion 84 is positioned on the downstream side in the rotational direction of the drive shaft 20 with respect to the discharge hole 83. A shortest distance D1 from the protruding portion 84 where a guide surface 85 is formed to the drive shaft 20 is preferably less than a distance D2 from a center O (or the center of gravity) of the discharge hole 83 to the drive shaft 20. Accordingly, the guide surface 85 easily comes into contact with the debris that moves in the rotation direction, and the debris can be effectively guided to the discharge hole 83. Alternatively, noting that the drive shaft 20 has a substantially cylindrical shape, and the outer peripheral surface thereof is a curved surface, even when the protruding portion 84 protrudes from the discharge hole 83 toward the drive shaft 20, the shortest distance D1 from the protruding portion 84 to the drive shaft 20 still can be equal to or longer than the distance D2 from the center O of the discharge hole 83 to the drive shaft 20. The distances D1 and D2 are not limited to any particular distance, and are, for example, approximately 1 mm.

A center line that passes through the centers of the passage 81 and the discharge hole 83 extends toward the central axis X of the drive shaft 20. The protruding portion 84 has the guide surface 85 that faces a direction that is opposite to the moving direction of the drive shaft 20 at its top. The guide surface 85 guides the debris discharged from the proximal opening portion 25 of the rotating drive shaft 20 to the discharge hole 83. The guide surface 85 is a surface that is continuous with the inner surface of the discharge hole 83. Alternatively, the guide surface 85 need not be a surface that is continuous with the inner surface of the discharge hole 83.

Further, the discharge port 80 has an auxiliary guide surface 86 that faces the distal side, on the proximal side of the discharge hole 83. The auxiliary guide surface 86 extends toward the drive shaft 20 from the discharge hole 83. The auxiliary guide surface 86 is formed in the protruding portion 84. Alternatively, the auxiliary guide surface 86 may be formed at a part different from the protruding portion 84 on which the guide surface 85 is formed. For example, the guide surface 85 may be a part of the inner surface on the proximal side of the discharge hole 83. When the discharge port 80 is inclined at the angle θ, a part of the surface continuous from the inner surface on the proximal side of the discharge hole 83 can be the auxiliary guide surface 86. Also, in a case where the discharge port 80 is inclined to the proximal side at the angle θ, a part of the auxiliary guide surface 86 extends to the distal side and can be positioned on the distal side rather than a proximal portion of the discharge hole 83.

The auxiliary guide surface 86 guides the debris discharged from the proximal opening portion 25 of the drive shaft 20 while the debris is moving in the proximal direction, to the discharge hole 83. The auxiliary guide surface 86 is a surface that is continuous with the inner surface of the discharge hole 83. Alternatively, the auxiliary guide surface 86 need not be a surface that is continuous with the inner surface of the discharge hole 83.

The auxiliary guide surface 86 is formed with a concave portion 86A that is recessed in an arc shape in a direction away from the drive shaft 20. Accordingly, since the concave portion 86A is positioned along the outer circumference of the drive shaft 20, the gap between the drive shaft 20 and the auxiliary guide surface 86 is smaller than that in a case where the concave portion 86A is not positioned along the outer circumference of the drive shaft 20, and the debris is easily guided to the discharge hole 83 by the auxiliary guide surface 86. A distance D3 from the auxiliary guide surface 86 to the drive shaft 20 is less than the distance D2 from the center O of the discharge hole 83 to the drive shaft 20. The distance D3 is not limited to any particular distance, and is, for example, approximately 1 mm.

The material of the discharge port 80 is not particularly limited, and, for example, polyolefin such as polyethylene, and polypropylene, polyester such as polyamide and polyethylene terephthalate, fluorine-based polymer such as ETFE, polyether ether ketone (PEEK), polyimide, and the like can be preferably used. Further, the discharge port 80 may be made of a plurality of materials, and a reinforcing member such as a wire rod may be embedded therein.

Next, the drive device 200 will be described.

As illustrated in FIG. 1, the drive device 200 includes a drive unit 220 that generates the rotational force and an aspiration unit 230 that generates the aspiration force.

The drive unit 220 includes the rotary drive shaft 221 and a first motor 222 that rotates the rotary drive shaft 221. The rotation speed of the first motor 222 is not particularly limited, and is, for example, 5,000 to 200,000 rpm.

The aspiration unit 230 includes the aspiration tube 231, a pump 232, a second motor 233, and a waste liquid pack 235. The aspiration tube 231 can be connected to the discharge port 80 of the medical device 10. The pump 232 is driven by the second motor 233 and applies a negative pressure to the aspiration tube 231. Further, the pump 232 discharges the fluid aspirated through the aspiration tube 231 to the waste liquid pack 235.

The configuration of the drive device 200 is not limited to the above-described example. For example, the mechanism for generating the rotational force and the mechanism for generating the aspiration force may be separate devices.

Next, a method of using the medical device 10 according to the first embodiment will be described by taking as an example a case of cutting and aspirating the lesion area such as thrombus and calcified lesion in a blood vessel.

First, the operator inserts a guide wire (not illustrated) into the blood vessel and makes the guide wire reach the vicinity of the lesion area. Next, the operator inserts a proximal end of the guide wire into the guide wire lumen 33 of the medical device 10. Then, the medical device 10 is maneuvered to reach the vicinity of the lesion area along the guide wire.

Next, as illustrated in FIG. 2, the operator connects the rotary drive shaft 221 of the drive device 200 to the rotation input unit 110. Subsequently, the operator connects the aspiration tube 231 to the discharge port 80. After this, the operator actuates the drive device 200. Accordingly, rotation of the rotary drive shaft 221 and aspiration of the aspiration tube 231 are started. The rotary drive shaft 221 rotates the rotation input unit 110. Accordingly, the proximal shaft 90 fixed to the rotation input unit 110 rotates, and the drive shaft 20 and the cutting portion 40 rotate together with the proximal shaft 90. The rotating cutting portion 40 cuts the lesion area in the blood vessel.

The aspiration tube 231 applies a negative pressure to the second internal space 66 via the discharge port 80. Therefore, the negative pressure is applied to the aspiration lumen 21 of the drive shaft 20 from the proximal opening portion 25 positioned in the second internal space 66. Therefore, as illustrated in FIG. 4, the lesion area cut by the blade 41 of the cutting portion 40 becomes debris and moves towards the inside of the cutting portion 40 to the proximal side. The debris is aspirated into the aspiration lumen 21 through the distal opening portion 26 of the drive shaft 20.

The aspirated debris passes through a proximal end of the drive shaft main body 22 and reaches the proximal opening portion 25, which is a side hole, as illustrated in FIGS. 2 and 3. The debris that has reached the proximal opening portion 25 is discharged from the proximal opening portion 25 into the second internal space 66. When the debris is discharged from the proximal opening portion 25, the debris moves in a direction away from the central axis X of the drive shaft 20 while moving toward the proximal side by inertial force. The proximal opening portion 25, which is a side hole, rotates the debris in the discharging direction. Therefore, when the debris is discharged from the proximal opening portion 25, the debris receives a rotational force from the inner wall surface of the drive shaft 20 and the vicinity of the proximal opening portion 25 and moves in the rotation direction of the drive shaft 20.

The debris discharged to the second internal space 66 is aspirated into the discharge hole 83, enters the passage of the discharge port 80, and is discharged to the aspiration tube 231. The proximal opening portion 25 is disposed at a distal portion of the second internal space 66, and the discharge hole 83 is also disposed at the distal portion of the second internal space 66. Therefore, the debris moving toward the proximal side can be discharged at the distal portion of the second internal space 66 and can be effectively aspirated by the discharge hole 83.

When the discharge hole 83 is disposed on the distal side or the proximal side of the length S along which the proximal opening portion 25 is positioned, the debris discharged from the proximal opening portion 25 easily gets caught on the edge of the proximal opening portion 25 and is easily spread around the rotating drive shaft 20. When the debris is spread around the drive shaft 20 in the vicinity of the proximal opening portion 25, the proximal opening portion 25 is blocked and the discharge of the debris is hindered. Therefore, the debris is retained in the second internal space 66 and becomes less likely to be discharged from the discharge port 80. On the other hand, in the present embodiment, at least a part of the discharge hole 83 overlaps at least a part of the length S along which the proximal opening portion 25 is positioned in the axial direction of the drive shaft 20. Accordingly, the aspiration force from the discharge hole 83 is directly applied to the proximal opening portion 25. Therefore, the debris discharged from the proximal opening portion 25 can smoothly enter the discharge hole 83. Therefore, the debris discharged from the proximal opening portion 25 becomes less likely to be spread around the rotating drive shaft 20. Therefore, the proximal opening portion 25 of the drive shaft 20 is prevented from being completely blocked by the debris. Therefore, the retention of the debris in the housing 60 is prevented, and the debris is effectively discharged from the discharge hole 83.

Further, the edge portion 25A on the distal side of the proximal opening portion 25 is formed substantially perpendicular to the central axis X. Therefore, the proximal opening portion 25 can secure a wide space on the distal side. Therefore, the proximal opening portion 25 can quickly discharge the debris that has moved in the aspiration lumen 21 to the proximal side and reached the proximal opening portion 25 into the housing 60, from the opening that is formed as wide as possible. The debris discharged into the housing 60 is quickly discharged to the outside through the discharge hole 83. Therefore, the debris is less likely to be spread around the proximal opening portion 25. Further, the edge portion 25B on the proximal side of the proximal opening portion 25 is formed by an arc that is convex toward the proximal side. Therefore, the proximal opening portion 25 can increase the strength by preventing the concentration of stress while securing a large space on the proximal side.

When the debris is discharged from the proximal opening portion 25, the debris receives a rotational force from the inner wall surface of the drive shaft 20 and the vicinity of the proximal opening portion 25 and moves in the rotation direction of the drive shaft 20. The debris that moves in the rotation direction of the drive shaft 20 is likely to come into contact with the guide surface 85 that faces a direction that is opposite to the moving direction of the drive shaft 20 at its top. The guide surface 85 guides the debris discharged from the proximal opening portion 25 of the rotating drive shaft 20 while moving in the rotational direction, to the discharge hole 83. The guide surface 85 is a surface that is continuous with the inner surface of the discharge hole 83. Therefore, the guide surface 85 can guide the debris discharged from the proximal opening portion smoothly to the discharge hole 83. Therefore, the proximal opening portion 25, which is the discharge port of the debris, is less likely to be blocked by the debris. Therefore, the debris is less likely to be retained in the housing 60, flows smoothly, and is discharged from the discharge port 80 to the outside.

Further, the end portion 82 of the discharge port 80 is formed with the protruding portion 84 only on one side of both sides, with the discharge hole 83 therebetween in the moving direction of the drive shaft 20 at its top. In other words, the discharge port 80 does not have a part that protrudes from the end portion 82 at a position that faces the guide surface 85 with the discharge hole 83 interposed therebetween. Therefore, the debris discharged from the proximal opening portion 25 while moving in the rotation direction of the drive shaft 20 can reach the guide surface 85 without being hindered from moving at a position that faces the guide surface 85 of the discharge port 80. Therefore, the debris is effectively guided to the discharge hole 83 by the guide surface 85 and discharged.

When the debris is discharged from the proximal opening portion 25, the debris moves in the proximal direction due to the inertial force generated when the debris moves inside of the drive shaft 20. The debris that moves in the proximal direction is likely to come into contact with the auxiliary guide surface 86 that is positioned on the proximal side of the proximal opening portion 25 and faces the distal side. The auxiliary guide surface 86 guides the debris discharged from the proximal opening portion 25 of the drive shaft 20 while moving in the proximal direction, to the discharge hole 83. The auxiliary guide surface 86 is a surface that is continuous with the inner surface of the discharge hole 83. Therefore, the auxiliary guide surface 86 can guide the debris discharged from the proximal opening portion 25 smoothly to the discharge hole 83. The auxiliary guide surface 86 is positioned on the proximal side from at least a part of the length S along which the proximal opening portion 25 is positioned. Therefore, the debris that is discharged from the proximal opening portion 25 on the distal side of the auxiliary guide surface 86 and moves in the proximal direction can be smoothly guided to the discharge hole 83 by the auxiliary guide surface 86. Further, when viewed in the axial direction of the drive shaft 20, the auxiliary guide surface 86 is formed with the concave portion 86A, and thus, the gap between the auxiliary guide surface 86 and the drive shaft 20 is small. Therefore, the debris discharged from the proximal opening portion 25 is prevented from moving to the proximal side from between the drive shaft 20 and the auxiliary guide surface 86. Therefore, the debris is effectively guided to the discharge hole 83 by the auxiliary guide surface 86.

Further, the extending direction Y of the passage 81 of the discharge port 80 is inclined toward the proximal side with respect to the plane Z orthogonal to the central axis X of the drive shaft 20. Therefore, the passage 81 and the discharge hole 83 can smoothly discharge the debris discharged from the proximal opening portion 25 while moving in the proximal direction, to the outside without significantly changing the direction.

The debris discharged to the outside from the discharge port 80 reaches the pump 232 through the aspiration tube 231. The debris that has reached the pump 232 is discharged to the waste liquid pack 235, as illustrated in FIG. 1. After the cutting of the lesion area and the aspiration of the debris are completed, the operator stops the operation of the drive device 200. Accordingly, the rotation of the drive shaft 20 is stopped and the aspiration of the pump 232 is stopped. As a result, the cutting by the cutting portion 40 and the discharge of the debris are stopped. After this, the medical device 10 is drawn out from the blood vessel, and the procedure is completed.

As described above, the medical device 10 according to the first embodiment is the medical device 10 for removing the object in the body lumen, including: the rotatable drive shaft 20 having the lumen; the cutting portion 40 fixed to the distal portion of the drive shaft 20 to cut the object; and the housing 60 that contains the proximal portion of the drive shaft 20 and has the discharge port 80 formed to discharge the cut object to the outside. The drive shaft 20 has the proximal opening portion 25 that partially opens in the circumferential direction on the proximal portion, and the discharge port 80 includes the discharge hole 83 that discharges the object discharged through the proximal opening portion 25 to the outside of the housing 60, and the guide surface 85 that protrudes toward the proximal opening portion 25 to the cut object to the discharge hole 83.

The medical device 10 configured as described above can guide the object that is discharged from the proximal opening portion 25 and rotates to change the discharging direction thereof, to the discharge hole 83 of the discharge port 80 by the guide surface 85. Therefore, the proximal opening portion 25 of the drive shaft 20 is prevented from being completely blocked by the object. Therefore, the medical device 10 can prevent the retention of the object produced when cutting the object in the body lumen, and effectively discharge the object.

In addition, the guide surface 85 faces the direction that is opposite to the moving direction of the drive shaft 20 at its top. Accordingly, the guide surface 85 easily receives the object that is discharged from the proximal opening portion 25 and rotates to change the discharging direction thereof, and thus, the object can be effectively guided to the discharge hole 83.

The guide surface 85 is positioned on the downstream side in the rotational direction of the drive shaft 20 with respect to at least a part of the discharge hole 83. Accordingly, the guide surface 85 can smoothly guide the object discharged from the proximal opening portion 25 to the discharge hole 83 of the discharge port 80.

Further, the discharge hole 83 is close to the distal portion of the proximal opening portion 25. Accordingly, the medical device 10 can quickly discharge the object immediately after the object is moved through the lumen of the drive shaft 20 in the proximal direction and discharged from the proximal opening portion 25, from the discharge hole 83. Therefore, the medical device 10 can prevent the retention of the object, and effectively discharge the object.

In addition, the guide surface 85 is a surface that is continuous with the inner surface of the discharge hole 83. Accordingly, the medical device 10 can effectively guide the object discharged from the proximal opening portion 25 of the drive shaft 20 from the guide surface 85 to the discharge hole 83. Therefore, the medical device 10 can prevent the retention of the object, and effectively discharge the object.

The discharge port 80 has the auxiliary guide surface 86 that faces the distal side, and at least a part of the auxiliary guide surface 86 is positioned on the proximal side of at least a part of the discharge hole 83. Accordingly, the medical device 10 can effectively guide the object discharged from the proximal opening portion 25 of the drive shaft 20 while moving in the proximal direction, to the discharge hole 83 with the auxiliary guide surface 86. Therefore, the medical device 10 can prevent the retention of the object, and effectively discharge the object. It should be noted that a part of the auxiliary guide surface 86 may be positioned on the distal side of a part of the discharge hole 83.

Further, the auxiliary guide surface 86 has the concave portion 86A on the side close to the drive shaft 20. Accordingly, the concave portion 86A of the auxiliary guide surface 86 can be placed close to the drive shaft 20 with a small gap. Therefore, the object discharged from the proximal opening portion 25 of the drive shaft 20 is less likely to move to the proximal side through the gap between the auxiliary guide surface 86 and the drive shaft 20. Therefore, the medical device 10 can effectively guide the object discharged from the proximal opening portion 25 to the discharge hole 83 with the auxiliary guide surface 86.

Second Embodiment

Figure 5:
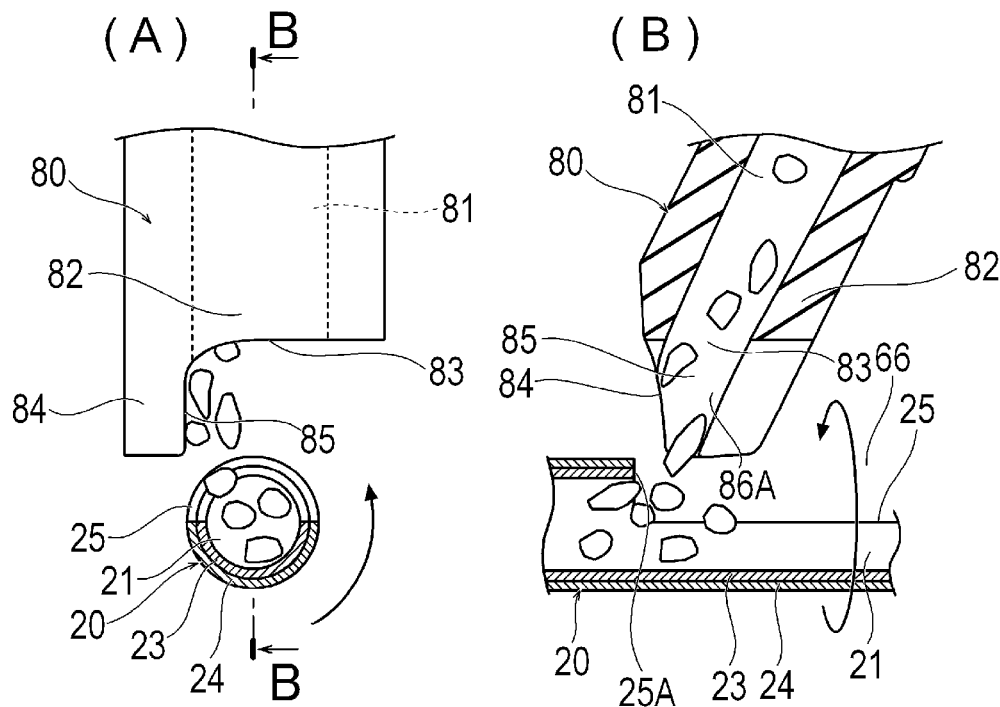
FIG. 5 is a view illustrating a proximal portion of a drive shaft and a discharge port according to a second embodiment.

As illustrated in FIG. 5, the medical device 10 according to a second embodiment is different from that of the first embodiment in that the discharge port 80 does not include the auxiliary guide surface 86. The parts having the same functions as those in the first embodiment will be given the same reference numerals, and the description thereof will not be repeated.

The discharge port 80 does not include the auxiliary guide surface 86 that faces the distal side, on the proximal side of the discharge hole 83. In other words, the discharge port 80 does not include a part that extends toward the drive shaft 20 from the discharge hole 83 and faces the distal side, on the proximal side of the discharge hole 83. Therefore, the discharge hole 83 can effectively aspirate the object that has moved to the proximal side of the discharge port 80 in the housing 60. Therefore, the medical device 10 can prevent the retention of the object in the housing 60 and can effectively discharge the debris.

Third Embodiment

Figure 6:
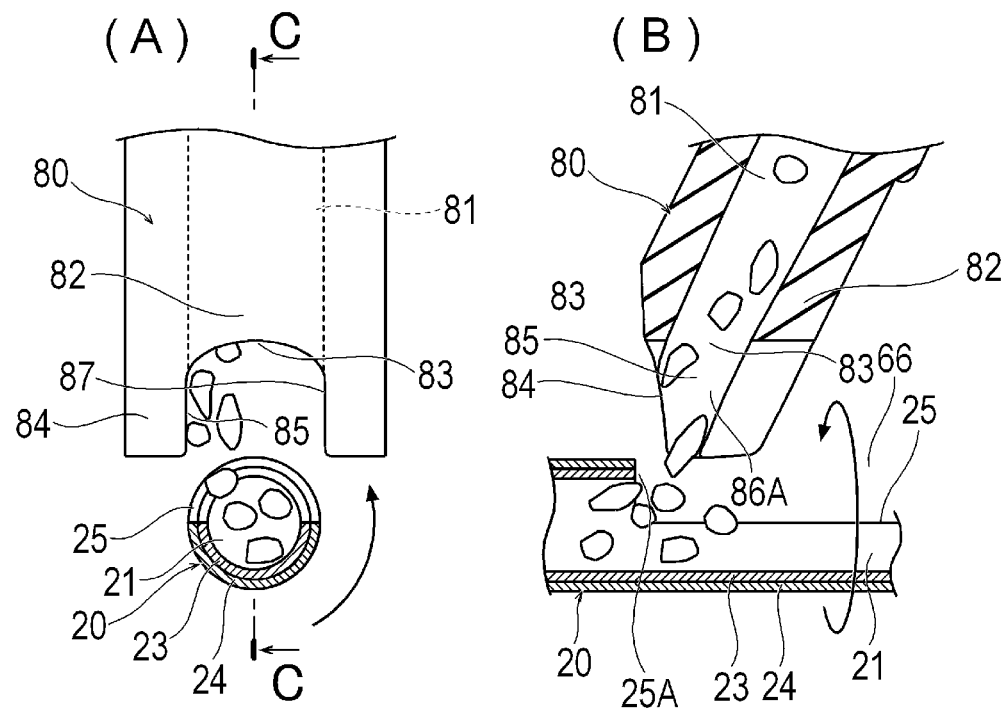
FIG. 6 is a view illustrating a proximal portion of a drive shaft and a discharge port according to a third embodiment.

As illustrated in FIG. 6, the medical device 10 according to a third embodiment is different from that of the first embodiment in that the discharge port 80 does not include the auxiliary guide surface 86 and has a facing surface 87. The parts having the same functions as those in the first embodiment will be given the same reference numerals, and the description thereof will not be repeated.

The discharge port 80 has the facing surface 87 that faces the same direction as the moving direction of the drive shaft 20 at the top. The facing surface 87 is a surface that is continuous with the inner surface of the discharge hole 83, and faces the guide surface 85. In other words, the facing surface 87 and the guide surface 85 are positioned substantially opposite to the inner surface of the discharge port 80 in the circumferential direction. The discharge port 80 does not include the auxiliary guide surface 86 (as in the second embodiment) that faces the distal side on the proximal side of the discharge hole 83, but may include the auxiliary guide surface 86.

As described above, the discharge port 80 has the facing surface 87 that faces the same direction as the moving direction the drive shaft 20 at its top. Accordingly, the medical device 10 regulates the flow of the object discharged from the proximal opening portion 25 between the guide surface 85 and the facing surface 87, and effectively discharge the object from the discharge hole 83.

Fourth Embodiment

Figure 7:
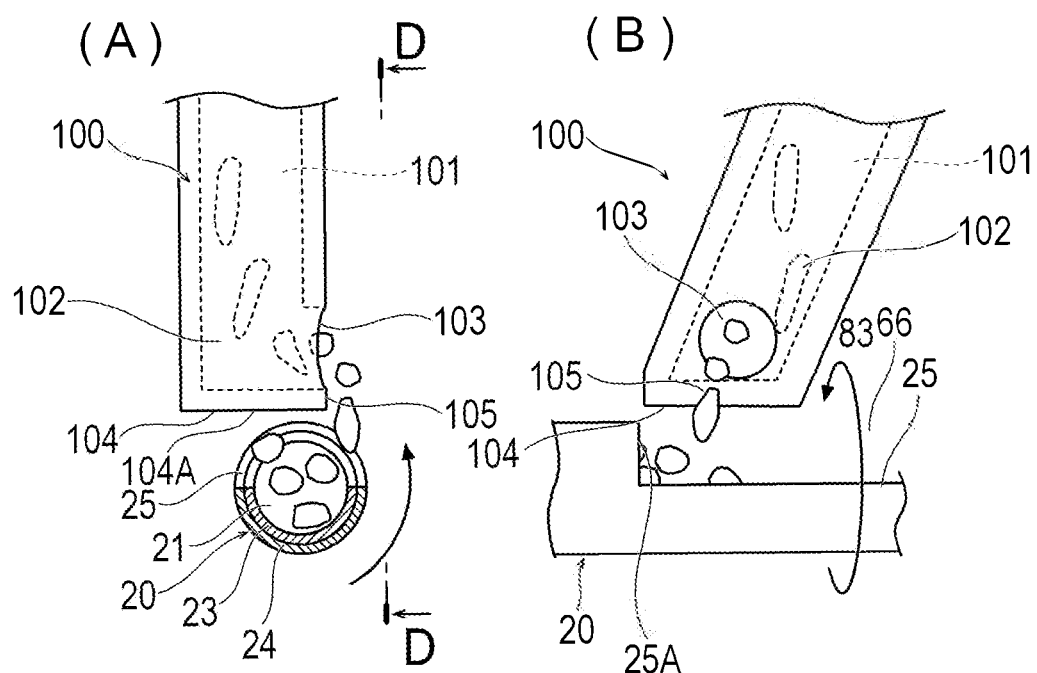
FIG. 7 is a view illustrating a proximal portion of a drive shaft and a discharge port according to a fourth embodiment.

As illustrated in FIG. 7, the medical device 10 according to a fourth embodiment is different from that of the first embodiment in the structure of a discharge port 100. The parts having the same functions as those in the first embodiment will be given the same reference numerals, and the description thereof will not be repeated.

The discharge port 100 has a substantially cylindrical shape, a first end portion thereof is positioned on the outside of the housing 60, and a second end portion thereof protrudes to the second internal space 66 of the housing 60. The discharge port 100 has a passage 101 that extends from the first end portion to the second end portion. An end portion 102 of the discharge port 100 that protrudes to the second internal space 66 has a discharge hole 103 on the outer peripheral surface instead of an end surface 104. The discharge hole 103 faces the direction that is opposite to the moving direction of the drive shaft 20 at its top. The outer peripheral surface of the discharge port 100 has a guide surface 105 between the discharge hole 103 and the end surface 104. The guide surface 105 faces the direction that is opposite to the moving direction of the drive shaft 20 at its top. A central portion 104A of the end surface 104, which is depicted in FIG. 7(A), is positioned so as to be biased toward the moving direction of the drive shaft 20 at its top with respect to the position of the central axis of the drive shaft 20. In other words, in the illustration of FIG. 7(A), the central portion 104A of the end surface 104 is further to the left than the central axis of the drive shaft 20.

As described above, the medical device 10 according to the fourth embodiment is the medical device 10 for removing the object in the body lumen, including: the rotatable drive shaft 20 having the lumen; the cutting portion 40 fixed to the distal portion of the drive shaft 20 to cut the object; and the housing 60 that contains the proximal portion of the drive shaft 20 and has the discharge port 80 formed to discharge the cut object to the outside. The drive shaft 20 has the proximal opening portion 25 that opens in the circumferential direction, and the discharge port 80 includes the discharge hole 83 on a surface of the discharge port 80 that faces the direction that is opposite the moving direction of the drive shaft 20 at its top and discharges the object discharged through the proximal opening portion 25 to the outside of the housing 60.

In the medical device 10 configured as described above, the object to be discharged from the proximal opening portion 25, that rotates to change the discharging direction thereof, is likely to be directly guided to the discharge hole 83 because the discharge hole 83 faces the direction that is opposite to the moving direction of the drive shaft 20 at its top. Therefore, the object can be easily discharged from the discharge hole 83 to the outside of the housing. Additionally, the proximal opening portion 25 of the drive shaft 20 is prevented from being completely blocked by the object. Therefore, the medical device 10 can prevent the retention of the object formed by cutting the object in the body lumen, and effectively discharge the object.

Further, the discharge hole 103 is opened toward the direction opposite to the moving direction of the drive shaft at its top, and the guide surface 105 is the outer peripheral surface of the discharge port 100 and positioned closer to the drive shaft 20 than the discharge hole 103. Accordingly, the discharge hole 103 is opened toward the direction opposite to the moving direction of the drive shaft at its top, and thus, the object discharged from the proximal opening portion 25 of the drive shaft 20 can easily enter the discharge hole 103. Furthermore, the object discharged from the proximal opening portion 25 of the drive shaft 20 is effectively guided to the discharge hole 103 from the guide surface 105 positioned on the outer peripheral surface of the discharge port 100. Therefore, the medical device 10 can prevent the retention of the object in the housing 60 and can effectively discharge the object. It should be noted that a part of the guide surface 105 may be positioned on a side of the discharge hole 103 farther from the drive shaft 20 than a part of the discharge hole 103. It should also be noted that the guide surface 105 may be positioned on opposite sides of the discharge hole 103 with respect to the moving direction of the drive shaft 20 at its top.

Further, the central portion 104A of the end surface 104 is positioned so as to be biased toward the moving direction of the drive shaft 20 at its top with respect to the position of the central axis of the drive shaft 20. Therefore, the discharge hole 103 formed on the outer peripheral surface of the cylindrical discharge port 100 can be disposed at a location where the object discharged from the proximal opening portion 25 can easily enter.

Fifth Embodiment

Figure 8:
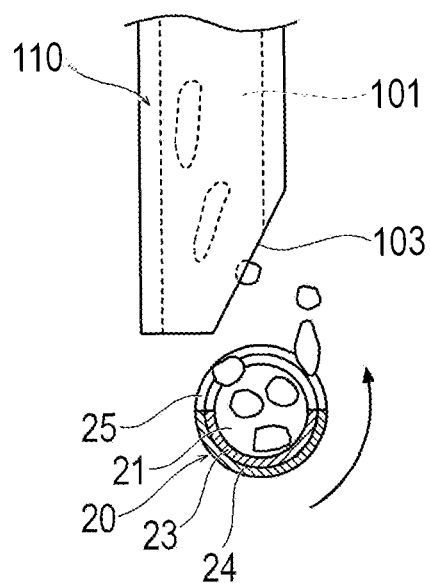
FIG. 8 is a cross-sectional view of a proximal portion of a drive shaft and a discharge port according to a fifth embodiment from the distal side.

As illustrated in FIG. 8, the medical device 10 according to a fifth embodiment is different from that of the first embodiment in the structure of a discharge port 100. The parts having the same functions as those in the first embodiment will be given the same reference numerals, and the description thereof will not be repeated.

The discharge port 100 is a cylinder, and the discharge hole 103 is formed by cutting a part of an opening end perpendicular to the axis of the cylinder obliquely with respect to the axis of the cylinder. The discharge hole 103 faces the direction opposite to the moving direction of the drive shaft 20 at its top. Therefore, in the discharge hole 103, in addition to the object discharged from the proximal opening portion 25, that changes its discharging direction by rotation, the object immediately after being discharged from the proximal opening portion 25 and before being rotated is likely to be directly guided to the discharge hole 103. It is thus possible to effectively receive the object into the discharge hole 103. Therefore, the discharge hole 103 can discharge the object from the proximal opening portion 25 to the outside of the housing 60.

Note that the present invention is not limited to the above-described embodiments, and various modifications are possible by those skilled in the art within the technical idea of the present invention. For example, the body lumen into which the medical device 10 is inserted is not limited to a blood vessel, and may be, for example, a vessel, a ureter, a bile duct, a fallopian tube, a hepatic duct, or the like. Further, the medical device 10 and the drive device 200 may be integrally configured.

Further, the discharge ports 80 and 100 may be formed integrally with another member (for example, the second part 62 or the like) of the housing 60.

Further, the aspiration force may be generated by the drive shaft instead of the aspiration unit 230 connected to the discharge ports 80 and 100. When the drive shaft has the structure of an Archimedean screw pump, it is possible to generate the aspiration force by rotating. In this case, the discharge ports 80 and 100 can discharge the debris even when the discharge ports 80 and 100 are not connected to the aspiration unit 230 that generates the aspiration force.

What is claimed is:

1. A medical device for removing an object in a body lumen, the medical device comprising:
    a rotatable drive shaft having a lumen;
    a cutting portion fixed to a distal portion of the drive shaft to cut the object; and
    a housing that contains a proximal portion of the drive shaft and has a discharge port above the proximal portion of the drive shaft and through which the cut object is discharged,
    wherein the drive shaft has a proximal opening portion that extends around a portion of a circumference of the drive shaft to expose a discharge opening for the cut object, and
    wherein the discharge port includes a discharge hole through which the cut object discharged through the discharge opening of the proximal opening portion is discharged from the housing, and a guide surface that protrudes toward the proximal opening portion to guide the cut object into the discharge hole.

2. The medical device according to claim 1,
    wherein the guide surface faces a direction that is opposite to a moving direction of the drive shaft at a top of the drive shaft.

3. The medical device according to claim 2,
    wherein the guide surface is positioned on a downstream side of a rotational direction of the drive shaft with respect to at least a part of the discharge hole.

4. The medical device according to claim 3,
    wherein the discharge hole is closer to a distal portion of the proximal opening portion than a proximal portion of the proximal opening portion.

5. The medical device according to claim 4,
    wherein the guide surface is a surface that is continuous with an inner surface of the discharge hole.

6. The medical device according to claim 5,
    wherein the discharge port further includes an auxiliary guide surface that faces a distal side, and
    wherein the auxiliary guide surface is positioned on a proximal side of the discharge hole.

7. The medical device according to claim 1,
    wherein the discharge port has a surface that faces a moving direction of the drive shaft at a top of the drive shaft.

8. The medical device according to claim 1,
    wherein a passage that extends outwardly from the discharge hole of the discharge port is inclined toward a proximal side with respect to a direction orthogonal to a rotation axis of the drive shaft.

9. A medical device for removing an object in a body lumen, the medical device comprising:
    a rotatable drive shaft having a lumen; and
    a housing that contains a proximal portion of the drive shaft and has a discharge port through which the cut object is discharged,
    wherein the drive shaft has a proximal opening portion that extends around a portion of a circumference of the drive shaft to expose a discharge opening for the cut object, and
    wherein the discharge port includes a discharge hole through which the cut object discharged through the discharge opening of the proximal opening portion is discharged from the housing, and a guide surface that protrudes toward the proximal opening portion to guide the cut object into the discharge hole.

10. A medical device for removing an object in a body lumen, the medical device comprising:
    a rotatable drive shaft having a lumen;
    a cutting portion fixed to a distal portion of the drive shaft to cut the object; and
    a housing that contains a proximal portion of the drive shaft and has a discharge port through which the cut object is discharged,
    wherein the drive shaft has a proximal opening portion that extends around a portion of a circumference of the drive shaft to expose a discharge opening for the cut object, and
    wherein the discharge port includes a discharge hole on a surface of the discharge port that faces a direction that is opposite to a moving direction of the drive shaft at a top of the drive shaft and through which the cut object discharged through the discharge opening of the proximal opening portion is discharged from the housing.

11. A method of removing an object in a body lumen, said method comprising:
    positioning a cutter fixed to a distal portion of a drive shaft to cut the object;
    rotating the drive shaft to cut the object with the cutter and aspirating the cut object into a lumen of the drive shaft;
    discharging the cut object in the lumen of the drive shaft to a housing that contains a proximal portion of the drive shaft, wherein the proximal portion of the drive shaft has a discharge opening for the cut object that extends around a portion of a circumference of the drive shaft; and further discharging the cut object through a discharge port of the housing, wherein the discharge port is located above the discharge opening of the drive shaft and includes a first guide surface protruding toward the discharge opening of the drive shaft to guide the cut object into a passage of the discharge port through which the cut object is further discharged.

12. The method according to claim 11,
wherein the first guide surface faces a direction that is opposite to a moving direction of the drive shaft at a top of the drive shaft.

13. The method according to claim 12,
wherein the discharge port further includes second guide surface that protrudes toward the discharge opening of the drive shaft and faces the second guide surface.

14. The method according to claim 12,
wherein the discharge port further includes an auxiliary guide surface that faces a distal side, and
wherein the auxiliary guide surface is positioned on a side of the passage that is closer to a proximal side of the passage than a distal side of the passage.

15. The method according to claim 11,
wherein the passage is positioned obliquely with respect to a rotational axis of the proximal portion of the drive shaft, so that the passage tilts toward a proximal side of the drive shaft away.

16. The method according to claim 15,
wherein an angle formed by the passage with respect to the rotational axis of the proximal portion of the drive shaft is 30 to 60 degrees.

17. The method according to claim 11,
wherein a lower end of the passage is closer to a distal portion of the discharge opening than a proximal portion of the discharge opening.

18. The method according to claim 11,
wherein the first guide surface is a surface that is continuous with an inner surface of the discharge port that defines the passage.

19. The method according to claim 11,
wherein the discharge opening extends a predetermined distance in an axial direction of the drive shaft, and
wherein the drive shaft at a distal end of the discharge opening has a surface that is perpendicular to the axial direction and at a proximal end of the discharge opening has a surface that is oblique with respect to the axial direction.

* * * * *